United States Patent
Dani et al.

(10) Patent No.: US 7,525,664 B2
(45) Date of Patent: Apr. 28, 2009

(54) DEVICE AND METHOD FOR OPTICAL DETECTING SUBSTANCES CONTAINED IN WASTE GASES OF CHEMICAL PROCESSES

(75) Inventors: Ines Dani, Lichtenau (DE); Wulf Grählert, Dresden (DE); Volkmar Hopfe, Kleingiesshübel (DE); Gerrit Mäder, Dresden (DE)

(73) Assignee: Fraunhofer-Gesellschaft zur Förderung der angewandten Forschung E.V., München (DE)

( * ) Notice: Subject to any disclaimer, the term of this patent is extended or adjusted under 35 U.S.C. 154(b) by 0 days.

(21) Appl. No.: 11/628,283

(22) PCT Filed: May 27, 2005

(86) PCT No.: PCT/DE2005/000985

§ 371 (c)(1),
(2), (4) Date: Jan. 25, 2007

(87) PCT Pub. No.: WO2005/119213

PCT Pub. Date: Dec. 15, 2005

(65) Prior Publication Data

US 2008/0011049 A1 Jan. 17, 2008

(30) Foreign Application Priority Data

Jun. 4, 2004 (DE) .................. 10 2004 028 420

(51) Int. Cl.
*G01N 21/00* (2006.01)
(52) U.S. Cl. .................................... 356/437
(58) Field of Classification Search .......... 356/436–438
See application file for complete search history.

(56) References Cited

U.S. PATENT DOCUMENTS 3,614,243 A   10/1971   Harvey (Continued)

FOREIGN PATENT DOCUMENTS

AT   002225 U1   5/1899

(Continued)

OTHER PUBLICATIONS

German Examination Report of Oct. 25, 2004 of German Application No. 10 2004 028 420.2.
International Search Report of PCt/DE2005/000985.

*Primary Examiner*—Tarifur Chowdhury
*Assistant Examiner*—Tara S Pajoohi
(74) *Attorney, Agent, or Firm*—Matthew B. Dernier, Esq.; Gibson & Dernier LLP (57) ABSTRACT

The invention relates to a device and a method for the optical detection of substances contained in exhaust gases of chemical processes, wherein exhaust gases are conducted all the way through a channel element that forms an optical measuring section; at the channel element there are two flanges, closed off to the ambient area, and at least one window element through which electromagnetic radiation for the optical detection can be directed from a radiation source to a optical detector through the channel element; a purge gas is fed through the flanges into the channel element, whereby with a purge gas led into one of the flanges a closed laminar purge gas flow is to be formed in the bottom area of the interior of the channel element.

19 Claims, 4 Drawing Sheets

U.S. PATENT DOCUMENTS

| | | | |
|---|---|---|---|
| 3,628,028 | A | 12/1971 | Thorsheim |
| 3,833,305 | A | 9/1974 | Porter et al. |
| 4,443,072 | A | 4/1984 | Ballard |
| 4,468,124 | A | 8/1984 | Berick |
| 4,543,815 | A | 10/1985 | Troup et al. |
| 4,736,103 | A | 4/1988 | Nelson et al. |
| 4,874,243 | A | 10/1989 | Perren |
| 5,120,129 | A * | 6/1992 | Farquharson et al. ....... 356/246 |
| 5,146,283 | A | 9/1992 | Parnoff et al. |
| 5,908,789 | A * | 6/1999 | Weckstrom ................ 436/133 |
| 2004/0058488 | A1 | 3/2004 | Arno |

FOREIGN PATENT DOCUMENTS

| | | |
|---|---|---|
| DE | 1598353 | 5/1966 |
| DE | 1993225 | 9/1968 |
| DE | 2044139 | 9/1970 |
| DE | 2742972 A1 | 9/1977 |
| DE | 4105190 | 2/1991 |
| DE | 9117135 U1 | 10/1991 |
| DE | 29509702 U1 | 6/1995 |
| DE | 19531263 A1 | 8/1995 |
| DE | 20022379 U1 | 6/2000 |
| EP | 0064200 A2 | 11/1982 |
| EP | 0208646 | 7/1986 |
| EP | 1070943 A1 | 1/2001 |
| EP | 0768525 | 6/2003 |
| JP | 05126738 | 5/1993 |
| WO | WO88/01737 | 3/1988 |
| WO | WO91/18277 | 11/1991 |

* cited by examiner

DEVICE AND METHOD FOR OPTICAL DETECTING SUBSTANCES CONTAINED IN WASTE GASES OF CHEMICAL PROCESSES

BACKGROUND OF THE INVENTION

The invention relates to a device and a method for the optical detection of substances contained in the exhaust gases of chemical processes where said substances are formed, released and transported as a component of an exhaust gas flow from a reaction or vacuum chamber in various chemical processes.

With conventional solutions it is normal practice to extract individual samples successively from the exhaust gas flow and to perform a corresponding detection in more or less large time intervals for the individual samples in each case. Subsequently, no time-proximal intervention in the individual process can take place.

The extraction of a partial flow from the overall exhaust gas flow is also disadvantageous. Here, the overall exhaust gas volume subjectable to detection is reduced and, in particular, the absolute volume of the substances to be detected is reduced accordingly, whose component can already be very small in any event. As a result, detection errors can occur that can be of such an extent that traces of even essential substances in the exhaust gas cannot be recognised or can be recognised with a great timing delay only. Due to the timing delay, unstable compounds (so-called intermediates) cannot be detected or can be detected with limitations only. The intermediates are often process-domineering, so that their correct verification can be particularly important for a process control.

With a continual detection, also on the optical route in the comprehensive exhaust gas flow as described for example in EP 0 768 525 B 1, solid particles and/or aggressive gases, which are frequently contained in the exhaust gas flow in a relative large volume therein, lead to considerable disadvantages.

Solid particles disturb not only the optical detection as such because, as a rule, they are not transparent for the individual electromagnetic radiation or are light-scattering and on the route through an optic measuring cell they frequently and optically block or obstruct the beam path of the radiation, but they are also a problem as a result of the frequent adhesion to the wall or also to windows within measuring cells. This causes a layer formation which leads to a reduction of the cross-section and this again leads to an increase of the flow velocity and to turbulence formation of the exhaust gas flow. The window scale deposit reduces the transmissivity and, subsequently, a cleaning and/or a replacement of windows is required within short time intervals.

As a result, a cleaning of measuring cells in more or less short time intervals is required which often do not coincide with cleaning or maintenance cycles of the process technology as required in any event. Downtime results in this way or at least a redundant additional measuring system is required. Both are undesirable from the aspect of costs.

SUMMARY OF THE INVENTION

It is therefore the task of the invention to be able to carry out the possibility of an in-situ and time-proximal detection of substances contained in exhaust gases of chemical processes, and which can be used in an operationally reliable manner over long periods of time and which enables a sufficiently precise monitoring of substances in an exhaust gas flow.

In accordance with one or more embodiments of the invention, the detection of substances can be performed time-proximal to the process in-situ, meaning, immediately in the exhaust gas itself. In this way, various types of substances and chemical compounds which are chemically reactive, corrosion-supporting or toxicologically objectionable, as is the case as for example with various chlorine or fluorine compounds, can also be easily detected. In addition, conclusions can be drawn with regard to the sequence of the chemical processes in each case when certain substances are detected or no longer detected, so that a corresponding influence can be imposed on the performance of the individual chemical process and the begin or a termination of the chemical process can be initiated. The detection can also be performed in a quantitative manner, so that the individual portions of substances in the exhaust gas flow can be detected and, as required, can be taken into consideration for a process control.

In this way, for example, a process, where the internal cleaning of a vacuum chamber is carried out by means of the production of plasma, can be terminated if and when a sufficient degree of purity within the vacuum chamber is registered. This can then be the case when, for further processes, critically gaseous or particle-shaped components are no longer contained in the detected exhaust gas flow and/or no reaction products in cleaning processes, so that the time required for such a cleaning operation can be limited to a minimum.

In accordance with one or more embodiments of the present invention, methods and apparatus are provided for the optical detection of substances contained in exhaust gases of chemical processes. The methods and apparatus contemplate exhaust gases conducted through a channel element forming an optical measuring section. At the channel element two flanges may be closed off to an ambient area with at least one window element in each case are connected. Electromagnetic radiation for the optical detection of the respective substances is directed from a radiation source to an optical detector through the two flanges. Additionally, a purge gas flows into the channel element through the flanges.

Advantageous embodiments and further developments of the invention can be attained with features designated in the independent and subordinated claims herein.

The solution according to the invention for the detection of substances contained in the exhaust gases of chemical processes is established in such a way that the entire exhaust gases to the greatest possible extent are conducted through a channel element forming an optical measuring section. Two flanges are arranged at this channel element which are closed off gas-seal-tight to the ambient atmosphere by means of at least one transparent window in each case.

Through the windows and flanges, electromagnetic radiation is conducted all the way through the channel element and impinges on an optical detector that is suitable for a substance analysis. With the help of this detector, at least one substance contained in the exhaust gas can also be quantitatively detected as far as possible.

Purge gas inlets are provided at the flanges, and through these inlets an inert gas and/or a purge gas with known consistency can be routed into the flanges. In this case, the purge gas input ensures that any substances contained in the exhaust gas, particularly solid particles, cannot deposit or accumulate on the surface of the window elements that are transparent for the electromagnetic radiation.

The purge gas flow into the flange, which is arranged in the direction of flow of the exhaust gas conducted through the channel element, is conducted and influenced here in such a way that, proceeding from the lead-in zone of this flange into the channel element, at least one predominantly laminar purge gas flow in the bottom zone of the channel element is formed, which forms a film practically, which, if at all, is only slightly contaminated with the exhaust gas to be actually detected, establishing a fluid type barrier and at the same time a transport medium for solid particles opposite the inner wall of the channel element, so that an adhesion leading to a layer formation can be prevented.

This purge gas flow is to be formed, as far as possible, over the entire length of the channel element and fill out a maximum of 20% of the free cross-section of the channel element.

The channel element can be aligned and dimensioned in such a way that the solid particles, subject to gravitational force, are entrained in a "swimming up manner" in the lower zone of the exhaust gas flow on the purge gas flow and are drawn off by way of a distally arranged outlet for exhaust gas from the channel element in order to be subjected to a subsequently arranged exhaust gas secondary treatment.

In this way, a large area of the free cross-section of the channel element is free from solid particles and, through the gas layer, only a very minor thinning of the exhaust gas occurs, if at all, in the area of the channel element used for the optical detection, with purge gas.

The essentially non-influenced cross-sectional area of the channel element should be used for the optical detection. Accordingly, the individual electromagnetic radiation should be conducted above the purge gas flow, meaning, the bottom zone and the solid particles entrained with this in the exhaust gas flow, in beam form.

In this way, at least the flange in the distal direction of the channel element should be arranged at a clearance from the bottom, as far above as possible.

The inlet of the electromagnetic radiation of a radiation source through a window element should also take place at a clearance above the bottom in the lead-in zone of the corresponding flange. In this case, an inclined beam routing preferably in the direction onto the optical detector should be preferred.

The longitudinal axis of the channel element, which essentially co-determines also the direction of flow of the exhaust gas flow through the channel element, should be aligned as horizontal as possible in order to be able to effectively utilise the gravitation acting on the solid particles. In certain cases, however, a gradient can also be allowed, which preferably enables a vertically declining exhaust gas flow. The gradient angle should be kept as small as possible and should not exceed 45°.

The proximally arranged flange, over which the purge gas flow in the channel element is formed, should have if possible no shoulder to the bottom zone of the channel element or should have no edge and should run out flush into the bottom zone of the channel element, so that gas flow turbulence can be avoided in this area.

In order to ensure the blockage effect of the purge gas in the flanges, through which an entrance of substances and particles from the exhaust gas into the flanges and all the way up to the window elements is to be avoided, the inlets for the purge gas into the flanges should be arranged at a clearance to the lead-in zone into the channel element and if possible also a clearance to the window elements. In this case, the free cross-section in the flanges, the volume flow of exhaust gas from the process, the purge gas volume flow as well as the flow velocities of the gases can be selected accordingly in order to avoid a fouling and/or a scale depositing of the window elements.

It is particularly advantageous to envisage two purge gas inlets in flanges arranged at a distance to one another. In this way, a veiling effect can be achieved with purge gas in front of the surface of window elements facing into the interior of the individual flange. In addition, and in this way, there is the possibility of influencing the flow of the purge gas from the flange in the direction of the channel element. In this case, a spiral-shaped circular flow of purge gas in the window zone of a flange has proved to be favourable.

In addition, the invention can be developed further where a control of purge gas supplied by way of flanges is carried out with due consideration of the individual exhaust gas volume flow and/or the flow velocity of the exhaust gas within the channel element in order to ensure the protection of the window elements during the various operating conditions, to avoid an adhesion of solid particles at the inner wall of the channel element, and to be able to maintain favourable conditions within the channel element for the optical detection.

It is advantageous to use pairs of window elements at each of the flanges, where there is a gap formed between said window elements.

In this case, an apparatus can be envisaged for the measurement and/or monitoring of the pressure within the gap between the window elements which acts together with an actuating device in each case for a closure element. Such an apparatus ensures here that, with pre-definable change of the internal pressure in the gap between the respective two window elements with a closure element, a gas-seal-tight closure of the channel element is realised.

In this way, such a closure element can close off the channel element in the zone of a pair of window elements if an increase or reduction of pressure is recognised within a gap between two window elements. A respective actuating device can be activated in such a way when pre-definable maximum or minimum internal pressures in the gap and/or a pre-definable pressure increase or pressure drop are detected.

This is then required as a rule if a corresponding damage has occurred to at least one window element or if a sealing element, that seals off the window elements against the channel element, has lost its gas seal-tight integrity.

The electromagnetic radiation in this case is conducted through the optical measuring section through the channel element in such a way that the individual pairs of window elements are arranged in the beam path of the electromagnetic radiation in each case.

The applied closure elements can be executed in the form of plate or swivel dampers. With reference to the window elements, they should be arranged if possible in the interior of the channel element and be sealed off gas-tight to the casing of the channel element. This has a particularly advantageous effect if, following destruction or as a result of ageing, the replacement of individual window or sealing elements is required and these are then accessible from the outside.

With such a gas-tight closure in these critical cases, and to a high degree of certainty, any aggressive and toxic substances can be prevented from escaping to the surrounding area or also, depending on the circumstances, ambient atmosphere can be prevented from penetrating a vacuum chamber or reaction chamber as a room for a performance of chemical processes.

As already indicated, the detection of the respective substances should be effected continually, in-situ and in an optical manner. For this purpose, a wavelength selective detection with correspondingly suitable optical detectors with usage for certain substances of specific absorption bands/lines or absorption spectrums is an appropriate choice. A detector suitable for this purpose is then arranged outside of the optical measuring section, the channel element behind a pair of optically transparent window elements, and detection can take place of the respective intensities of substance-specifically selected wavelengths from the spectrum of electromagnetic radiation directed through the optical measuring section.

In this way, for example, a Fourier transformation infrared spectroscopy (FTIR) can be performed. For this purpose, a conventional interferometer in conjunction with a suitable radiation source for electromagnetic radiation can be applied.

There is also, however, the possibility of applying a correspondingly suitable radiation source for electromagnetic radiation which emits an adequately large wavelength spectrum, in conjunction with a spectrometer, known as such, for the optical detection of substances, as such, contained in exhaust gases and also their individual constituents (concentration) in the exhaust gas. Alternatively, monochromatic radiation sources, which are tunable in an adequately broad wavelength range, can be applied together with conventional radiation detectors.

The beam path of the individual electromagnetic radiation and the two pairs of window elements should be aligned and arranged as best as possible in such a way that an immediate influence caused by particle-shaped components, which are contained in the exhaust gas, can be avoided.

In addition and for this case, it can be also be purposeful to conduct correspondingly the exhaust gas flow into, through and out of the channel element whereby, despite everything, it should be ensured that also a detection of such solid particles is possible.

The already mentioned beam path of the electromagnetic radiation as applied for the optical detection through the optical measuring section of the channel element can be conducted advantageously above the vertical lower bottom of the channel element, whereby it is particularly advantageous to align this in the opposite direction to the direction of flow of the exhaust gas flow through the channel element, in a correspondingly gradient angle from above to below. In the latter case, a pair of window elements should be arranged in the immediate vicinity of the bottom of a channel element arranged vertically below and, respectively, the other pair of window elements arranged at a certain distance from the vertical lower bottom of the channel element, in a certain height therefore, preferably in the zone of the vertical upper wall of the channel element, whereby the arrangement of the window elements can take into consideration the dimensioning and/or alignment of the individual flange with reference to the channel element.

In order to at least achieve a reduction of the influence of solid particles on the detection, there is the possibility of increasing at least section-wise the free inner cross-section of the channel element, thorough which the exhaust gas flow is conducted, so that a reduction of the flow velocity of the suctioned exhaust gas leads to a gravimetrical separation of the particles from the exhaust gas. In this way, for example, a channel element can be formed, having a free cross-section increasing the inner cone with it in the direction of flow of the exhaust gas.

Leakage losses in the window intermediate zone cannot be completely avoided. For this reason, it is advantageous to set a constant internal pressure within the gap between the pairs of window elements and, as required, to carry out an inspection of the seal-tight condition of both windows. For this purpose and for example by way of a corresponding supply line, a control valve or a normal valve in combination with a pressure sensor, a gas can be routed into the gap between pairs of window elements if, for example, leakage losses occur. For the input, a gas such as nitrogen can be applied which is inert and does not influence the optical detection.

In a further development of the invention, however, there is also the possibility of supplying a gas with known composition (calibration gas) at certain intervals into one or even both gaps between pairs of window elements, and to perform over a certain period of time a calibration of the optical measuring technology with the help of individual components contained in such a gas as well as their known concentrations in each case.

After the calibration has been performed, this gas can then be suctioned off again and filling can be carried out with an inert gas, non-critical for the detection, of the individual gap between window elements with a corresponding pressure.

For most of the substances to be detected, a corresponding radiation source which emits electromagnetic radiation in the wavelength range of the infrared and/or proximal infrared light, and a corresponding detector unit can be applied. For some gases, emitting radiation sources in the visible and ultraviolet spectral range can also be advantageously applied.

The device according to the invention, as already implied at the beginning, can be adopted in various applications. It is particularly suitable for the detection of exhaust gases coming from vacuum or reaction chambers as used for various types of surface modification techniques of workpieces. In such vacuum chambers the most varying types of CVD- or PVD methods or etching processes, known as such, can be carried out whereby, with the device according to the invention, a detection can be applied with actual surface modification processes such as the formation of surface coatings, surface structures as well as for interim-arranged cleaning processes for vacuum chambers.

Detection can be carried out in various pressure ranges within channel elements, whereby relatively wide pressure intervals are allowable in each case. In this way for example, detections can be performed if pressures above 0 to 500 mbar are registered in channel elements connected up to vacuum chambers. However, the method can be applied also in the atmospheric and gauge pressure ranges. Here it is advantageous, simultaneously with the detection of selected substances contained in the exhaust gas, to determine and to duly consider the respective internal pressure in the channel element and/or the flow velocity of the exhaust gas conducted through the channel element.

The device according to the invention can be operated with a high degree of safety and reliability, whereby a long-term application is possible without the necessity of maintenance or cleaning work.

Other aspects, features, and advantages of the present invention will be apparent to one skilled in the art from the description herein taken in conjunction with the accompanying drawings.

BRIEF DESCRIPTION OF THE DRAWING

The invention is to be explained as follows in greater detail in an exemplary manner. The drawings show the following.

DETAILED DESCRIPTION OF THE INVENTION

Figure 1:
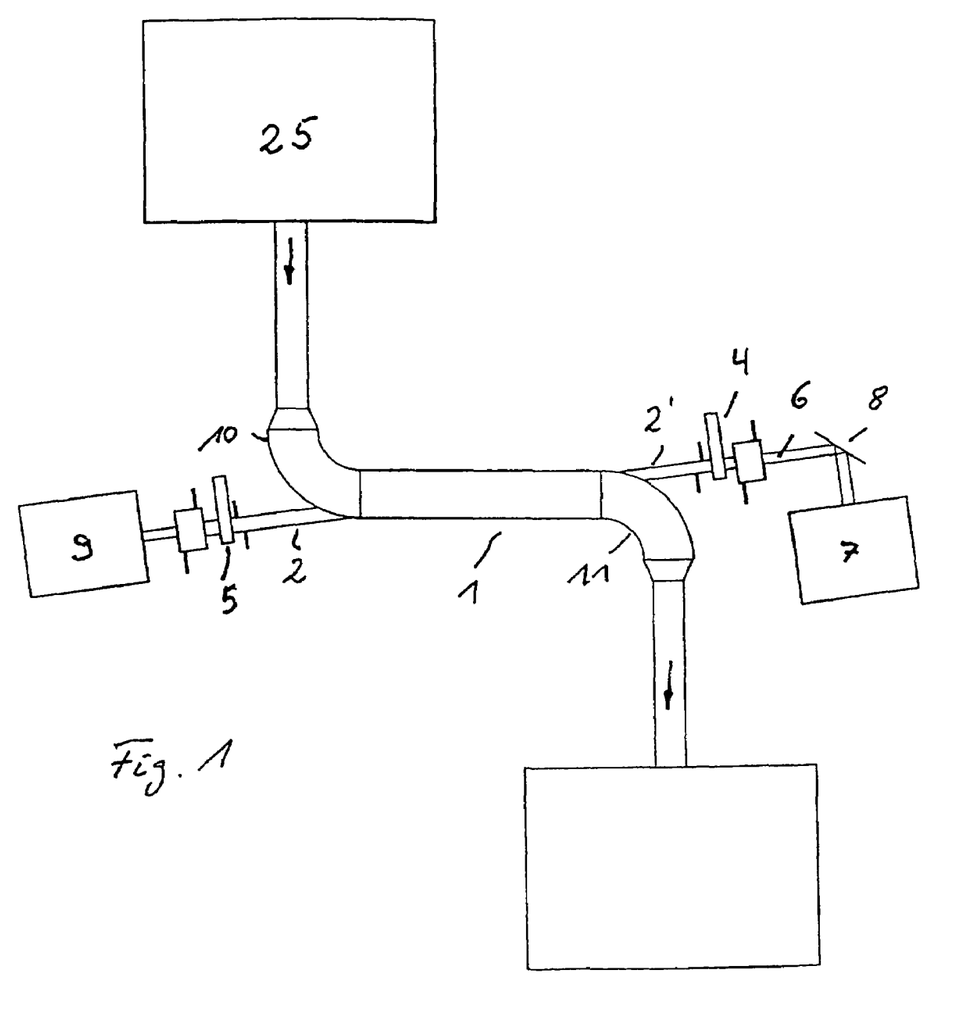
FIG. 1: in schematic arrangement, an example of a device according to the invention for the performance of a detection by means of FTIR-spectroscopy.

FIG. 1 shows in a schematic arrangement an example of a device according to the invention where the detection of substances contained in exhaust gases can be carried out by means of FTIR-spectroscopy.

The device shown in FIG. 1 uses a cylindrically shaped channel element 1 in this case, with a proximally arranged inlet for exhaust gas 10 from a vacuum chamber 25 and an outlet for the exhaust gas 11.

The channel element 1 has, between inlet and outlet 10 and 11 for exhaust gas, a length of 1000 mm and an internal diameter of at least 30 mm.

On the right-hand face side here of the channel element 1, there is a flange 2' with a closure element 4 between the outlet 11 for exhaust gas and the actual face-side, whereby a gas seal-tight closure has been ensured between channel element 1 and the ambient area. Outside thereof, there is a radiation source 7 for electromagnetic radiation 6 which is directed at the optical detector 7 by way of a reflecting element 8 through the flange 2', window elements 3.1, 3.2 (FIG. 3) arranged in the flange, the channel element 1 and the flange 2'.

On the left side of the channel element 1, ahead of the inlet 10 for exhaust gas, the flange 2 is again arranged in analogue form with window elements 3.1 and 3.2 as well as a closure element 5.

The channel element 1 in this example is aligned parallel to the horizontal, and this applies at least for that particular part that is used for optical detection.

In FIG. 1, the illustration of the inlet of purge gas into the flanges 2 and 2' and the purge gas flow within the channel element 1 are not shown, however, it is clear that the flange 2 in the zone of the inlet 10 for exhaust gas in the vertical lower part of the channel element 1 and the oppositely arranged flange 2' in the upper zone are connected to the channel element 1. This has an advantageous effect on the practically disturbance-free withdrawal of solid particles with the exhaust gas and the optical conditions during detection as the electromagnetic radiation 6 is routed in a corresponding gradient angle from above to below through the channel element 1.

An internal pressure in the range of, preferably, 0.1 to 100 mbar can exist within the channel element 1.

The flanges 2 and 2' should have a length which ensures that, between the lead-in of the flanges 2 and 2' into the channel element 1 and window element 3.1 and 3.2, respectively, a clearance of approx. 200 mm is maintained in each case.

Figure 2:
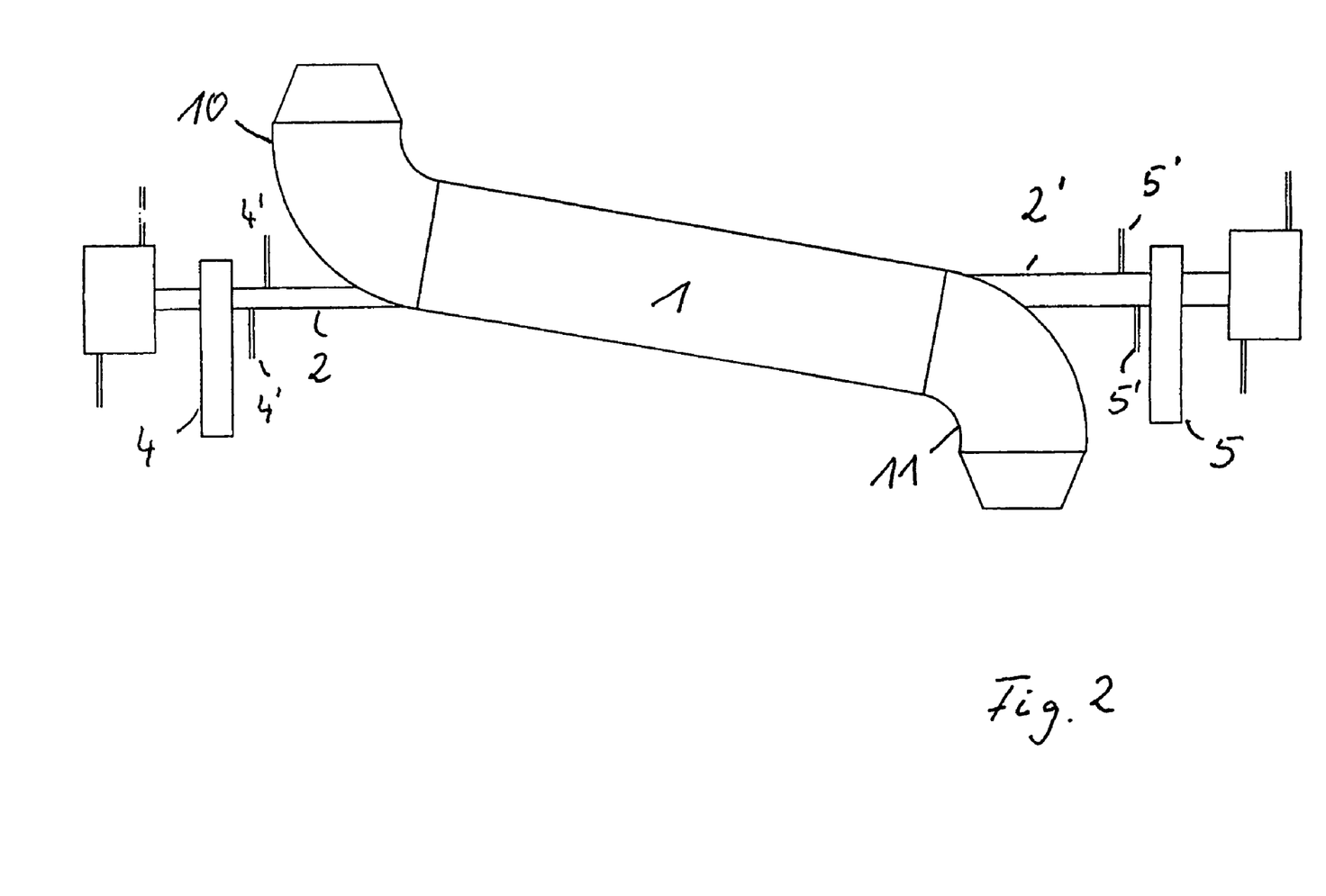
FIG. 2: in schematic arrangement, a second example with a gradient channel element with reference to the horizontal plane.

With FIG. 2 an inclined arrangement of a channel element 1 opposite the horizontal is to be indicated, with which the exhaust gas flow can flow through the channel element 1 with a corresponding gradient.

Moreover, it is to be particularly elucidated with FIG. 2 that, at the flanges 2 and 2', additional closure elements 4 and 5 can be arranged which can be closed as required, meaning, in damage situations or in time periods where no optical detection is to be carried out. With the help of the closure elements 4 and 5, in the first instance, a protection of the window elements 3.1 and 3.2 against fouling caused by adhesion can be achieved. In addition, a gas seal-tight sealing can be obtained if, for example, leakage has occurred in the subsequently arranged zone of the flanges 2 and 2' and/or at the window elements 3.1 and 3.2.

In the zone of the flanges 2 and 2', ahead of the closure elements 4 and 5 and with reference to the direction of the channel element 1, purge gas inlets 4' and 5' are also arranged with this example, through which a purge gas can be supplied if and when the closure elements 4 and 5 keep the flanges closed.

Attention is also drawn to the fact that, although not illustrated in FIG. 1, the window elements 3.1 and 3.2 in the radiation direction of the electromagnetic radiation 6 can have differently large dimensions. In this way, the window elements 3.1 and 3.2 which are arranged at the flange 2', meaning in the vicinity of the radiation source 7, should be significantly smaller than the window elements 3.1 and 3.2 which are arranged in the direction onto the detector 9 at the flange 2. The first-mentioned window elements 3.1 and 3.2 should so have a diameter of approx. 25 mm, and the window elements 3.1 and 3.2 arranged in the direction onto the detector a diameter of approx. 40 mm.

In both examples as shown, the beam path 6 of the respective electromagnetic radiation follows an axis, inclined from above to below, with reference to the longitudinal axis of the channel element 1.

Figure 3:
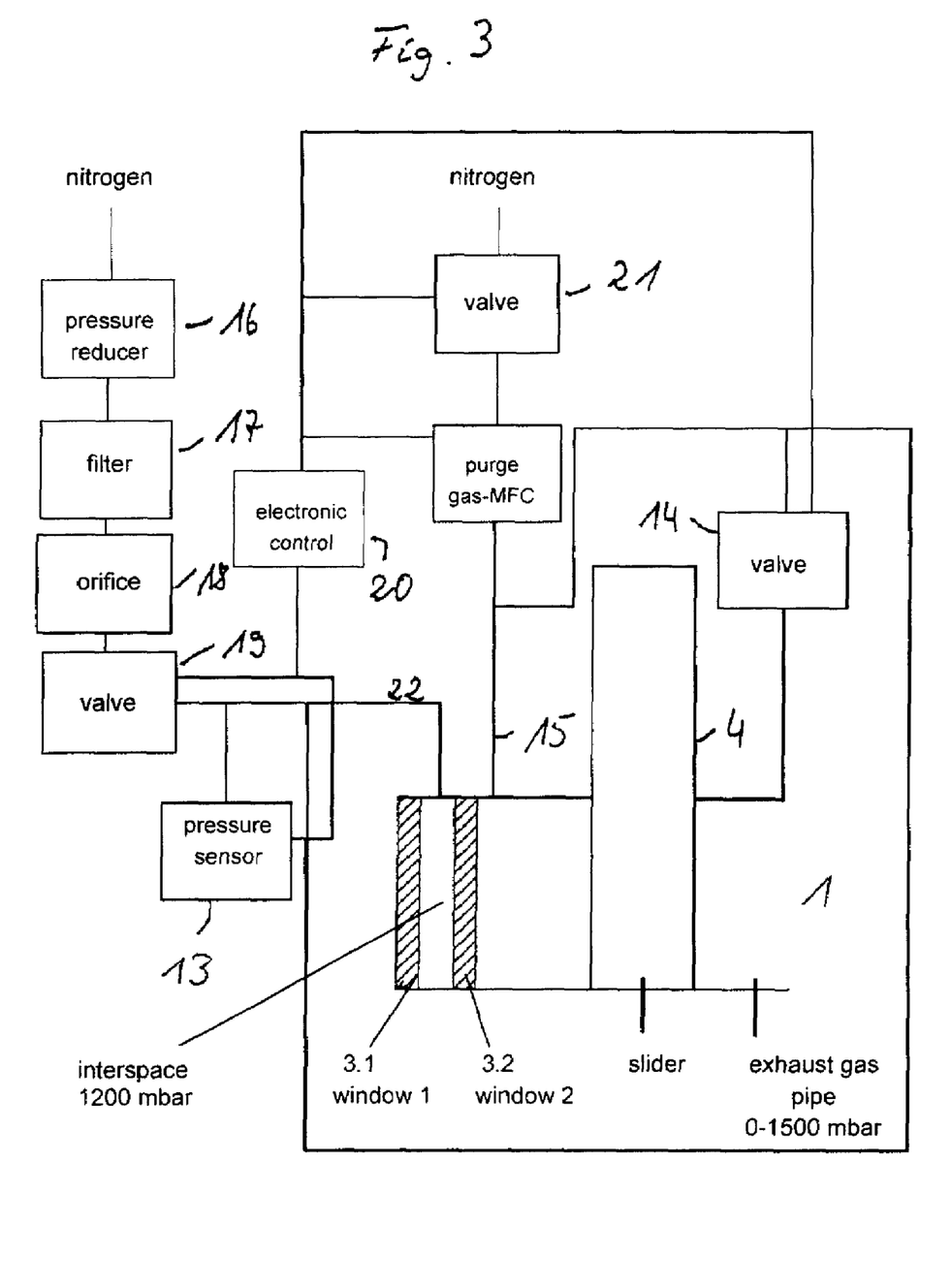
FIG. 3: in schematic arrangement, a block circuit diagram with elements for the determination of internal pressures, the input of various gases and for the actuation of a closure element.

The block circuit diagram shown in FIG. 3 is intended to elucidate in an exemplary manner the varying functions for parts that can be applied to a device according to the invention.

Therefore, only two transparent window elements 3.1 and 3.2 are shown here with a gap lying in between. In the gap between the window elements 3.1 and 3.2, and by means of a supply of an inert gas such as nitrogen for example, a constant pressure can be set, here 1200 mbar for example. The setting of the internal pressure in the gap between window elements 3.1 and 3.2 can be effected with the help of a pressure reducer 16 connected to a pressure gas vessel, a filter 17, an orifice 18 restricting the gas flow, a valve 19 and a pressure sensor 13.

Moreover, the pressure sensor 13 can detect a change of the internal pressure in the gap, as mentioned in the general part of the description, and can transmit this change to an electronic control 20.

If a pressure change exceeding a correspondingly predefinable value is detected, the valve 14 can be activated by means of the control 20, where this valve 14 again activates the respective closure element 4 or 5 at the flange 2 or 2' for the purpose of obtaining a gas seal-tight closure of the channel element 1 with reference to the ambient area.

In FIG. 3, an input of nitrogen as a suitable purge gas into the channel element 1 is shown in schematic arrangement. This again can take place by means of a valve 21 activated with the electronic control 20, where said valve 21 is connected to a pressure gas vessel, and by way of inputs 15. The input 15 for such a purge gas is arranged here in the immediate vicinity of the surface of the window element 3.2 facing into the interior of the channel element 1.

Figure 4:
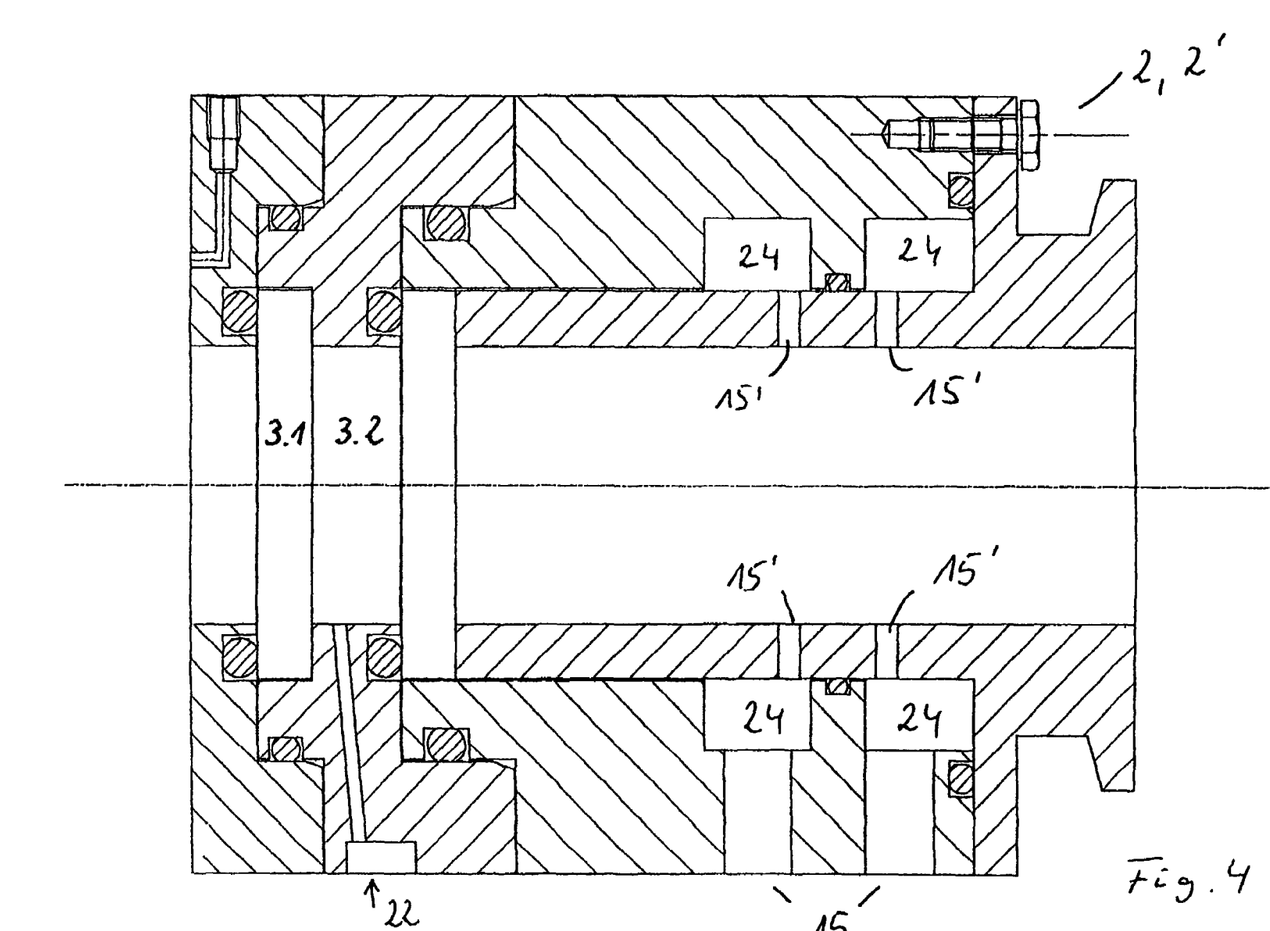
FIG. 4: in schematic arrangement, a flange connectable to a channel element with two window elements separated from one another with a gap, as well as inputs for purge gas.

FIG. 4 shows a flange 2 or 2' which can be connected to a channel element 1, such as that shown in FIGS. 1-2, and can be joined to this in a gas-seal-tight manner.

Such a flange 2 and 2', respectively, can be a carrier for two transparent window elements 3.1 and 3.2 which are arranged to one another with a gap lying in between and are closed off gas-seal-tight within the flange 2 or 2' by means of corresponding seals, and secured to a channel element 1.

At flange 2 or 2', one or several channels are formed which represent a fluid connection between the gap that is formed between the window elements 3.1 and 3.2, and the line 22. By way of this line 22, and by feeding in a corresponding gas, a constant internal pressure can be set in the gap as well as performing a detection of the internal pressure in the gap, and with a correspondingly detected change as already explained in the explanatory statement with reference to FIG. 3, an activation of a closure element 5 (not shown here) can be obtained.

Furthermore, and at the flange 2 or 2' shown here, there are also connections for a supply line 15 through which the purge gas can be fed in.

These supply lines 15 are joined to one or, as shown, two ring chamber(s) 24 going around a part of the flange 2 or 2'. Through the purge gas inlets 15' a purge gas can be entered into the interior of the flange 2 or 2' that communicates with the channel element 1.

The purge gas inlets 15' are arranged here in a clearance to the surface of the window element 3.2 facing inwards, and here again in two planes which are at a distance to one another, so that pressure and flow conditions can be set which prevent an immediate occurrence of particle-shaped components and, if the case arises, also other components contained in the exhaust gas that attack the surface of the window element 3.2.

In addition, purge gas is to be entered through the flange 2 into the channel element 1 in such a way that the laminar purge gas flow can form in the bottom zone of the channel element 1, with which a disturbance-free withdrawal of solid particles is attainable.

The window elements 3.1 and 3.2 are selected in such a way that they are transparent for the respective electromagnetic radiation used for the optical detection in the wavelength range of interest.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A device for the optical detection of substances contained in exhaust gases of chemical processes, the device comprising:
   a channel element forming an optical measuring section and through which the exhaust gases are conducted;
   two flanges closed off to an ambient area and disposed at opposing ends of the channel element, wherein a first of the two flanges opens into a bottom area of an interior of the channel element and a second of the two flanges opens into a top area of an interior of the channel element;
   at least one window element connected to each flange; and
   an optical detector,
   wherein electromagnetic radiation is directed from a radiation source to the optical detector through the flanges at the opposing ends of the channel element, through the at least one respective window element for each flange, and through the channel element in a gradient angle inclined with respect to a horizontal reference for the optical detection of the substances and with respect to a longitudinal axis of the channel element, from above to below, and a purge gas flows into the channel element through the flanges, and wherein
   one of the flanges is arranged in a zone of entry of the exhaust gas into the channel element and leads into the bottom area of the interior of the channel element in such a way that the purge gas exiting from the one of the flanges flows into a flow direction of the exhaust gas into the channel element and that, with the purge gas fed into the one of the flanges and exiting from the one of the flanges, a closed laminar purge gas flow is formed in the bottom area of the interior of the channel element and in the flow direction of the exhaust gas.

2. The device according to claim 1, wherein at least one purge gas inlet is arranged in a spaced apart relationship to a lead-in area of the flange.

3. The device according to claim 1, wherein the longitudinal axis of the channel element is one of: horizontally aligned, or inclined in a vertical direction at a maximum angle of up to about 45° with reference to a horizontal.

4. The device according to claim 1, wherein the purge gas emerging from the one of the flanges in the flow direction of the exhaust gas, and purge gas emerging from the other flange opposite to the flow direction of the exhaust gas, flows into the channel element.

5. The device according to claim 1, wherein the channel element has an increasing internal cross-section in a flow direction of the exhaust gas.

6. The device according to claim 1, further comprising a device for setting a constant internal gas pressure is disposed at a gap between the two window elements.

7. The device according to claim 1, further comprising inlets for providing inert purge gas are arranged in a plurality of planes in front of the window elements.

8. The device according to claims 1, wherein the channel element is connected to a vacuum chamber.

9. The device according to claim 1, wherein the radiation source emits electromagnetic radiation in an infrared, or near infrared, wavelength.

10. The device according to claim 1, wherein the device is connected to a control/regulation system for the chemical process.

11. A method for the optical detection of substances contained in exhaust gases of chemical processes, comprising:
   flowing exhaust gases through a channel element that operates as an optical measuring section;
   directing electromagnetic radiation in a gradient angle inclined with respect to a horizontal reference and with respect to a longitudinal axis of the channel element, from above to below, through two flanges, at least one respective window element connected to each of the two flanges, and through the exhaust gas and the channel element at an optical detector, wherein the two flanges are closed off to an ambient area and disposed at opposing ends of the channel element, and wherein a first of the two flanges opens into a bottom area of the channel element and a second of the two flanges opens into a top area of the channel element; and
   forming a closed laminar purge gas flow in the bottom area of an interior of the channel element and in a flow direction of the exhaust gas by means of a purge gas fed into the first of the two flanges and exiting from the first of the two flanges into the channel element parallel to the exhaust gas flow, thereby preventing an adhesion of solid substances contained in the exhaust gas to an inner wall of the channel element, wherein
   the first of the two flanges is arranged in a zone of entry of the exhaust gas into the channel element and leads into the bottom area of the interior of the channel element in such a way that the purge gas exiting from the first of the two flanges flows into the flow direction of the exhaust gas into the channel element.

12. The method according to claim 11, wherein an inert purge gas and/or a purge gas of known consistency is fed into the channel element.

13. The method according to claim 11, wherein the purge gas in the channel element fills out a maximum of about 20% of a free cross-section in the bottom area.

14. The method according to claim 11, wherein purge gas also flows into the channel element by way of a second flange forming a optical connection for the electromagnetic radiation from a radiation source.

15. The method according to claim 11, further comprising: providing a flange at each end of the channel element, at least one window element, and two purge gas inlets in the flanges spaced with respect to each other and spaced in front of the at least one window element.

16. The method according to claim 15, further comprising forming a spirally shaped circulating purge gas flow within the flanges in front of the window elements.

17. The method according to claim 11, wherein the purge gas flow is regulated in dependence on respective exhaust gas volume flow and/or a flow velocity of the exhaust gas in the channel element.

18. The method according to claim 11, further comprising performing an absorption spectroscopic detection for at least one substance contained in the exhaust gas.

19. The method according to claim 11, wherein the chemical process is regulated by means of the detection results.

* * * * *